(12) United States Patent
Shelton et al.

(10) Patent No.: US 7,758,567 B2
(45) Date of Patent: Jul. 20, 2010

(54) MEDICAL DEVICE INCLUDING PROCESSOR RUNNING INDEPENDENT PROCESSES TO COOPERATIVELY CONTROL THERAPY

(75) Inventors: Brian M. Shelton, Northridge, CA (US); Sam W. Bowman, Valencia, CA (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 661 days.

(21) Appl. No.: 11/176,857

(22) Filed: Jul. 7, 2005

(65) Prior Publication Data

US 2006/0009921 A1 Jan. 12, 2006

Related U.S. Application Data

(60) Provisional application No. 60/586,911, filed on Jul. 9, 2004.

(51) Int. Cl.
*A61B 5/04* (2006.01)
*A61F 7/12* (2006.01)
(52) U.S. Cl. .............. 604/890.1; 604/891.1; 604/892.1; 700/282
(58) Field of Classification Search .............. 604/890.1, 604/891.1, 892.1, 131, 246; 700/282
See application file for complete search history.

(56) References Cited

U.S. PATENT DOCUMENTS

| | | | | |
|---|---|---|---|---|
| 4,146,029 A | * | 3/1979 | Ellinwood, Jr. | ........... 604/891.1 |
| 4,424,812 A | * | 1/1984 | Lesnick | ......................... 607/30 |
| 4,731,051 A | | 3/1988 | Fischell | |
| 5,022,395 A | | 6/1991 | Russie | |
| 5,312,443 A | * | 5/1994 | Adams et al. | ................... 607/5 |
| 5,464,435 A | * | 11/1995 | Neumann | ....................... 607/9 |
| 6,175,881 B1 | | 1/2001 | Tanagawa | |
| 6,236,888 B1 | | 5/2001 | Thompson | |
| 6,400,985 B1 | * | 6/2002 | Amely-Velez | .................. 607/9 |
| 6,434,425 B1 | | 8/2002 | Thompson | |
| 6,464,687 B1 | * | 10/2002 | Ishikawa et al. | ......... 604/891.1 |
| 6,562,001 B2 | | 5/2003 | Lebel et al. | |

(Continued)

FOREIGN PATENT DOCUMENTS

WO    WO 03/009207 A1    1/2003

OTHER PUBLICATIONS

"Dependable Computer and Online Testing in Adaptive and Configurable Systems" -Saxena et al, Stanford University, IEEE Jan.-Mar. 2000.*

(Continued)

*Primary Examiner*—Michael D Masinick

(57) ABSTRACT

A medical system comprising an implantable medical device and an external controller. The medical device includes a therapy administration subsystem, a telemetry subsystem, and a control subsystem which includes a microprocessor operable in response to data and/or code provided via said telemetry subsystem for producing an output signal for controlling said therapy administration subsystem. The controller includes a user input means and a telemetry subsystem responsive to said user input means for communicating data and/or code to said medical device telemetry subsystem. The medical device control subsystem includes program means for causing said microprocessor to separately execute at least two software processes to respectively produce separate therapy control output components. Combinatorial logic means responds to the separate output components to produce the output signal for controlling the therapy administration subsystem.

16 Claims, 10 Drawing Sheets

U.S. PATENT DOCUMENTS

| | | |
|---|---|---|
| 6,571,128 B2 | 5/2003 | Lebel et al. |
| 6,577,899 B2 | 6/2003 | Lebel et al. |
| 6,648,821 B2 | 11/2003 | Lebel et al. |
| 7,079,977 B2 * | 7/2006 | Osorio et al. ............... 702/176 |
| 7,096,343 B1 * | 8/2006 | Berenbaum et al. ........... 712/24 |
| 2001/0041831 A1 | 11/2001 | Starkweather et al. |
| 2002/0022798 A1 * | 2/2002 | Connelly et al. ......... 604/93.01 |
| 2002/0035383 A1 | 3/2002 | Thompson |
| 2002/0058906 A1 | 5/2002 | Lebel et al. |
| 2002/0065540 A1 | 5/2002 | Lebel et al. |
| 2002/0198513 A1 | 12/2002 | Lebel et al. |
| 2003/0055406 A1 | 3/2003 | Lebel et al. |
| 2006/0020295 A1 * | 1/2006 | Brockway et al. ............. 607/17 |

OTHER PUBLICATIONS

"Implantable Pacemakers", Sanders et al, IEEE vol. 84, No. 3, Mar. 1996.*

* cited by examiner

Let:
   Vote 4 = $V_4$
   Vote 3 = $V_3$
   Vote 2 = $V_2$
   Vote 1 = $V_1$

Then:
   $S.3 = 0$
   $S.2 = ((V_1 \oplus V_2)(V_3 \oplus V_4)(V_1 V_2 \oplus V_3 V_4)) \oplus (V_1 V_2 V_3 V_4)$
   $S.1 = ((V_1 \oplus V_2)(V_3 \oplus V_4)) \oplus (V_1 V_2 \oplus V_3 V_4)$
   $S.0 = V_1 \oplus V_2 \oplus V_3 \oplus V_4$ Where:
   $(V_1 \oplus V_2) = (V_1 \text{ XOR } V_2)$
   $(V_1 V_2) = (V_1 \text{ AND } V_2)$

MEDICAL DEVICE INCLUDING PROCESSOR RUNNING INDEPENDENT PROCESSES TO COOPERATIVELY CONTROL THERAPY

RELATED APPLICATIONS

This application claims the benefit of U.S. Provisional Application 60/586,911 filed on 9 Jul. 2004 which is incorporated herein by reference.

FIELD OF THE INVENTION

This invention relates generally to medical devices of the type which include a microprocessor, or microcontroller, and more particularly to such devices, and methods of operation, configured to enhance patient safety and device reliability.

BACKGROUND OF THE INVENTION

Ambulatory medical devices, such as medication delivery devices, or infusion pumps, are designed and implemented to operate reliably over long periods to assure patient safety. To satisfy this requirement, it is common practice to build some "redundancy" into the device in order to eliminate single-point failure modes. For example, in some such devices intended to deliver a certain therapy to a patient, e.g., medication, it is known to incorporate two or more microprocessors (which term, as used herein, is intended to encompass microcontrollers) configured to independently perform duplicate functions. For example, note U.S. Pat. No. 6,648,821 which describes:

> An implantable infusion pump possesses operational functionality that is, at least in part, controlled by software operating in two processor ICs which are configured to perform some different and some duplicate functions. The pump exchanges messages with an external device via telemetry. Each processor controls a different part of the drug infusion mechanism such that both processors must agree on the appropriateness of drug delivery for infusion to occur.

SUMMARY OF THE INVENTION

The present invention is based on the realization that the redundancy benefits derived from using multiple microprocessors are mitigated by the increased part count, increased energy consumption, and increase in the number of potential failure modes attributable to the use of multiple microprocessors. Consequently, embodiments of the present invention are configured to better achieve the benefits of redundancy and the elimination of single point failure modes, by running multiple separate software processes on a single, or common, microprocessor.

More particularly, medical devices in accordance with the invention are configured to avoid a single point failure from causing an unsafe therapy condition, e.g., delivery of a therapeutically unsafe medication dosage, by utilizing a single microprocessor to separately execute two or more software processes. The processes are functionally duplicative, at least in part, with each producing a separate therapy control output component. The output components are then combined, preferably in hardware, based on predefined combinatorial logic, to produce an output signal for controlling a therapy administration subsystem, e.g., a medication pump mechanism.

In accordance with a preferred embodiment of the invention, the medical device single microprocessor operates in conjunction with a kernel memory to execute separate therapy control processes for producing separate output components, e.g., pump activation signals. For simplicity of explanation, it will be assumed herein that two separate processes are used but it should be understood that a greater number can be employed. The processes preferably use separate memories, e.g., a Process 1 memory and a Process 2 memory.

A medical device in accordance with the invention includes a control subsystem configured to produce a therapy control output signal for controlling a therapy administration subsystem. The control subsystem is characterized by (1) a microprocessor programmed to execute at least first and second processes to respectively produce first and second therapy control output components and (2) combinatorial logic means responsive to the first and second control output components for producing a therapy control output signal. The combinatorial logic means is implemented as a voting circuit which can be configured for unanimous or threshold voting.

In accordance with one significant aspect of a preferred control subsystem embodiment, the microprocessor includes at least two oscillators where the second oscillator functions to verify that the first, or primary, oscillator is operating at the correct frequency. This configuration prevents a single oscillator fault from affecting the time base of both processes which could otherwise produce a therapeutically unsafe condition; e.g., over-delivery of medication.

In accordance with another significant aspect of a preferred control subsystem embodiment, data used by the two processes to produce the respective control output components are maintained in duplicate. This is accomplished in a first implementation by configuring an external controller to transfer duplicate copies of data to the medical device control subsystem. In an alternative implementation, the external controller transfers a single copy together with a check value, e.g., checksum or CRC. When duplicate data is transferred, each software process uses a different copy. Where non-duplicate data is transferred, each process verifies the check value before copying the data into its local memory.

An exemplary preferred embodiment of the invention, to be described hereinafter, comprises an implantable medication delivery device in which separate processes (i.e., a Process 1, or "pump enable", and a Process 2, or "pump fire") are executed to produce respective output components for initiating a pump stroke to deliver a unit volume of medication to the patient.

BRIEF DESCRIPTION OF THE FIGURES

FIG. 4A depicts the execution of Kernel tasks and FIG. 4C depicts the execution of Process (1 and/or 2) tasks for a preferred implantable medication delivery device (schematically represented in FIG. 4B) to initiate a pump mechanism stroke for delivering a unit of medication to the patient;

DETAILED DESCRIPTION

Figure 1:
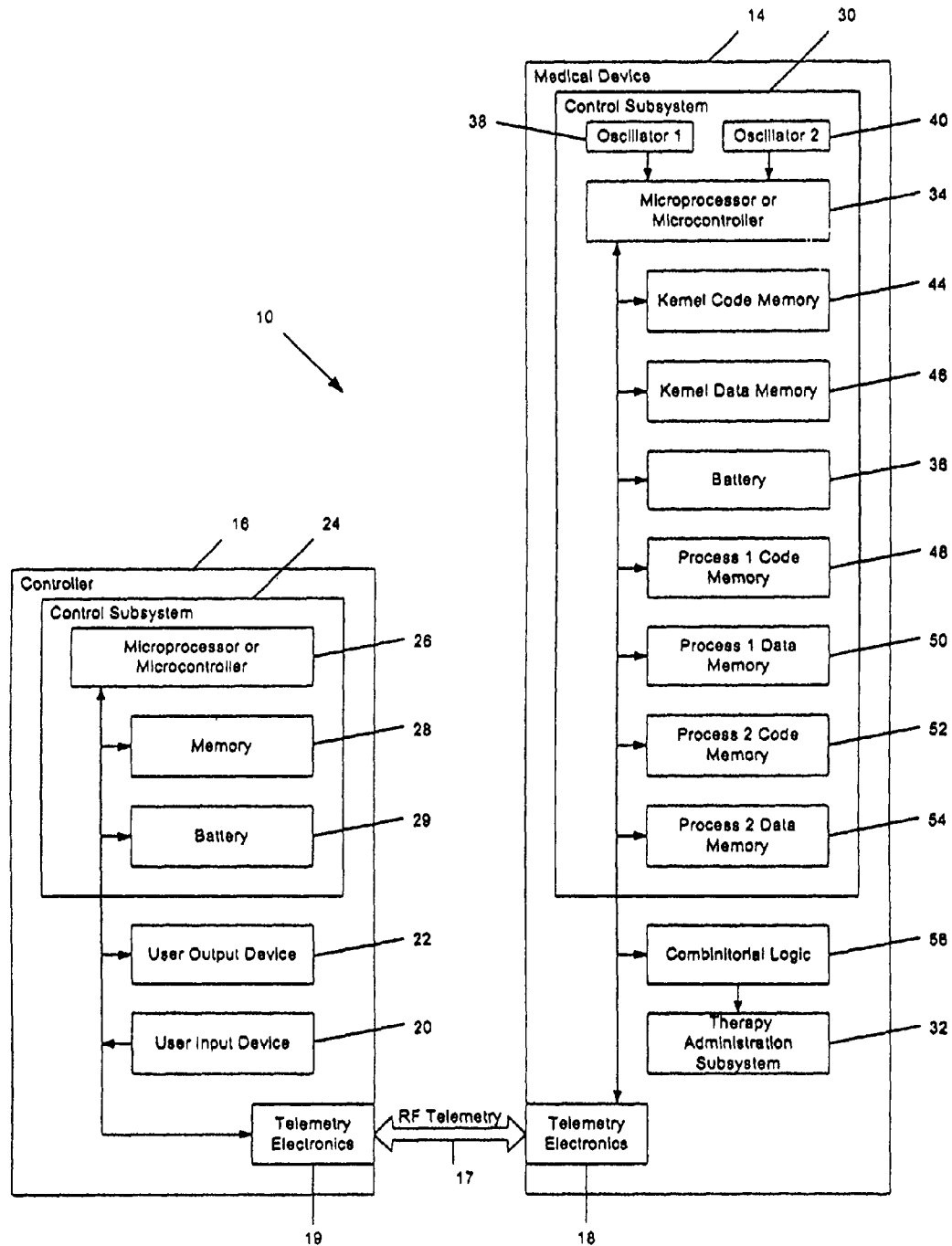
FIG. 1 is a block diagram of a medical system in accordance with the invention comprised of (1) at least one implantable device which includes a control subsystem for executing separate software processes to produce output signal components for controlling a therapy administration subsystem and (2) an external communication device, e.g. a controller, operable by a clinician and/or patient for programming the implanted device.

Attention is initially directed to FIG. 1 which comprises a generalized block diagram of a medical system 10 employing the teachings of the present invention. The system 10 is basically comprised of at least one medical device 14 and a communication device, e.g., a portable programmer, or controller, 16. The system of FIG. 1 contemplates that the controller 16 and the medical device 14 communicate wirelessly, e.g., via RF telemetry 17 using telemetry subsystem 18 and telemetry subsystem 19 respectively contained with the devices 14 and 16.

The medical device 14 can be configured for use internal or external to a patient's body. However, in the more significant applications of the present invention, the medical device 14 is implanted in a patient's body to perform some therapeutic function, such as controlled medication, i.e., drug delivery, or nerve stimulation. The controller 16, on the other hand, is intended to be deployed external to the body and for use by a physician or clinician or patient to generate control and data signals for transmission to the medical device 14. For example, using the controller 16, a clinician is able to produce command signals which are transmitted via RF link 17 to the medical device 14 to program its operation, i.e., affect its therapeutic performance such as by modifying its drug delivery profile. The present invention is particularly directed to the architecture and method of operation of the medical system 10 to enhance reliability and thus the safe administration of therapy.

By way of background, it should be understood that embodiments of the invention are intended to avoid any single-point failure from causing a change in therapy or the administration of excessive therapy, e.g., the over-delivery of medication by the implanted device. It is preferable to address all potential failures in the system, not just failures in the implanted device. The safe assumption is that errors can occur anywhere in the system, e.g., where therapeutic information is input by the clinician, in the memories of the external and implanted devices storing this information, in the software on both devices that handle this information, in the microprocessors (ALU, registers, and on-chip memory) of these devices, in the transmission that is sent between the two devices, and in the hardware that is used to administer the therapy.

More particularly, an exemplary point of failure involves the user input of the therapeutic control parameters via controller 16. To mitigate corruption of this information, embodiments of the invention are configured to immediately display the information to the user for verification. Thus, embodiments of the present invention preferably implement a procedure substantially as follows:

1. The user enters a therapeutic control parameter into external controller 16.
2. The software of the external device immediately makes a duplicate copy of the data and checks to verify that the two copies of the data match.
3. The software then displays the duplicate copy so that the user sees what is saved in the copy rather than what he entered. Thus the user is immediately aware if an error occurs.

Another potential point of failure is in the memories of the external and implanted devices. If a memory location suffers from some latent defect, it is possible for either the data (e.g., therapeutic control parameters) or the software that handles this data to become corrupted. Thus, anything that is stored in memory should either be stored in duplicate or with a validation code (e.g., CRC) to avoid allowing a single bit memory error to cause an unsafe device action. In order to protect communication between the external and implanted devices, the data in messages should either be transmitted in duplicate or with a validation code. The safest and simplest of schemes is to transmit whatever is stored. In other words, if the data is stored in duplicate, both copies of the data should be transmitted allowing each of the software processes executed in device 14 to use a different copy. In the case of parameters that are delivered to device 14 with a validation code, each process should validate the data prior to use. Whenever the therapeutic parameters are changed within the implanted device, it is preferable to perform the following steps:

1. The Kernel's message handler copies all of the received therapeutic parameters into a common storage area.
2. The Kernel notifies the multiple therapeutic administration processes that new parameters and/or parameter block have been received.
3. Each process checks the validation codes for all blocks and parameters that were not received in duplicate.
4. If the block or parameter is valid, each process will copy the block or parameter into its local memory.
5. If the block or parameter is invalid, the process will flag or send an error code to the Kernel and will prevent changes in therapy.
6. Each process can use duplicate parameters either by accessing them from a common storage area or by copying these parameters into its local memory.

Because only one microprocessor is used in the implanted device 14, the processes must use some of the same resources. The duplication of parameters and voting of the multiple processes does not prevent a hardware failure in a shared resource from impacting the administration of medical therapy. Therefore, all shared resources should be tested. For example, the clock that is used to time the therapeutic administration should be tested, for example, by using a different clock that is driven by a different oscillator. Further, the microprocessor ALU, its feed, and its result registers are examples of other potential single-point failure sources. These are preferably tested by executing all of the known instructions of the microprocessor using pre-selected test operands and comparing the results against pre-computed test results.

In accordance with the invention multiple software processes are executed in the device 14 to produce multiple output components which are then used in a voting procedure. Voting is preferably performed in hardware so there is no single point in the software where a decision is made to administer or change the therapy. A simple voting scheme could use an AND gate to combine the delivery signals from the two processes. The multiple processes must coordinate their voting. Using one processor and one clock for the processes is advantageous because this makes coordinating their votes relatively simple.

A preferred system which functions in accordance with the foregoing to enhance patient safety will be described in detail hereinafter with respect to an exemplary drug delivery system wherein the implanted device 14 includes an actuatable pump. In such a system, one process can function to signal the pump mechanism to fire and another process can function to enable that firing of the pump mechanism. It is preferable to define uniform accumulation and delivery intervals, e.g., a one minute accumulation interval and a 500 ms delivery interval, so that each process can indicate a certain number of pump strokes to be initiated at the beginning of each accumulation interval and can signal a pump stroke during the appropriate delivery intervals.

With continuing reference to FIG. 1, the controller 16 is preferably comprised of a user input device 20, e.g., a keyboard, a user output device 22, e.g., a display, and a control subsystem 24. The subsystem 24 includes a microprocessor 26, a memory 28, and a power source, e.g., battery 29. The control subsystem 24 functions to control telemetry communication between controller 16 and medical device 14 to, for example, enable a user input via input device 20 to provide parameter information and program the medical device 14 to affect its operation.

The medical device 14 in accordance with the present invention includes a control subsystem 30 for controlling a subsystem 32 which administers patient therapy, e.g., medication delivery. The control subsystem 30 includes a microprocessor (or microcontroller) 34, a power source, e.g., battery 36, a first oscillator 38, a second oscillator 40, and a system memory. For clarity of explanation herein, the system memory can be considered to be functionally partitioned into a Kernel memory comprising a code portion 44 and a data portion 46, a Process 1 memory comprising a code portion 48 and a data portion 50, and a Process 2 memory comprising a code portion 52 and a data portion 54. As will be discussed hereinafter, the medical device microprocessor 34 operates in conjunction with the aforementioned memory portions to execute multiple separate processes (which for convenience in explanation will be assumed to be two), i.e., Process 1 and Process 2, to respectively produce separate output components which are applied to combinatorial logic 56. The combinatorial logic 56 responds to the respective output components to produce a therapy control output signal for controlling the therapy administration subsystem 32.

Figure 2A:
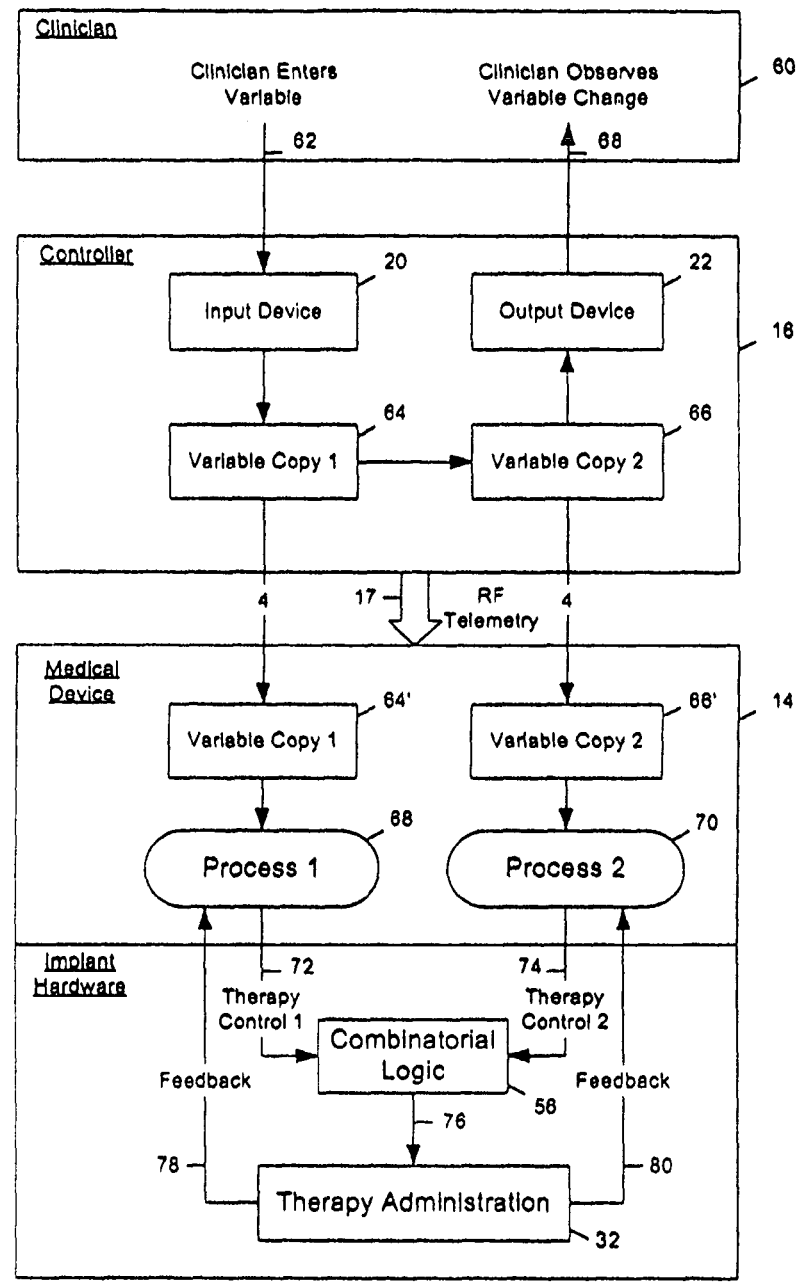
FIG. 2A is a block/flow diagram depicting a preferred technique for responding to controller inputs to produce duplicate parameter data, in accordance with the present invention, for use by the separate processes.

Attention is now directed to FIG. 2A which comprises a high level block/flow diagram depicting a preferred scheme for executing first and second redundant processes. Block 60 represents the actions of a clinician working in conjunction with the controller 16 to enter a variable for use by the medical device 14. More particularly, the clinician enters a variable 62 using the controller input device 20. The controller stores a first variable copy in memory at 64 and produces a clone or duplicate variable copy stored at 66. The duplicate variable copy stored at 66 drives the controller output device 22 to display the entered variable to the clinician at 68. Thus, if one of the variable copies is corrupted during this process, immediate feedback will be provided to the clinician to give him the opportunity to correct the error.

The stored variable copies 64, 66 are communicated via RF telemetry 17 to the medical device 14 and respectively stored as variable copies 64' and 66' in the Process 1 and Process 2 data memories (FIG. 1). The variable copies 64' and 66' are then used by two separate software processes, represented at 68 and 70 in FIG. 2A, when executed by the microprocessor 34 (FIG. 1). The Execution of Process 1 produces a first therapy control output component 72 and the execution Process 2 produces a second therapy control output component 74. These components 72, 74 are applied to combinatorial logic 56 which comprises a voting mechanism to produce a resultant therapy control output signal 76 for controlling the therapy administration subsystem 32. Although, the exemplary embodiments illustrated herein only show the utilization of two separate processes, alternative embodiments in accordance with the invention could execute a greater number of separate processes, e.g., four. The combinatorial logic 56 can be implemented in a variety of ways, as exemplified in FIGS. 7A, 7B, 7C to require, for example, a unanimous vote of the applied components or a lesser threshold, e.g., 75%. Regardless, as depicted in FIG. 2A, it is preferable to feedback the result produced by the logic 56 to the processes 68, 70 as represented by paths 78 and 80.

Figure 2B:
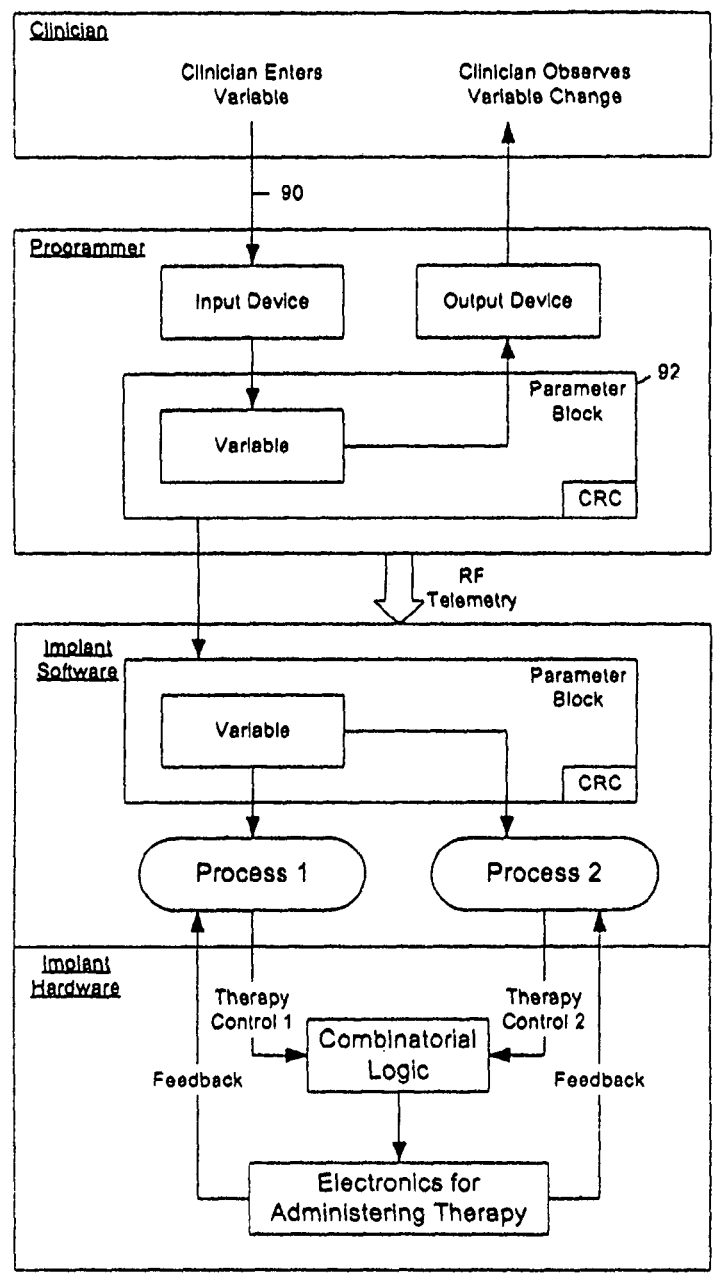
FIG. 2B is a block/flow diagram depicting an alternative technique for responding to controller inputs to produce verified parameter data for use by the separate processes.

Attention is now directed to FIG. 2B which illustrates a scheme alternative to that shown in FIG. 2A. In the scheme of FIG. 2B, the controller 16 instead of producing a duplicate copy of the input variable, attaches a check value, e.g., checksum or CRC, to the variable. More particularly, note in FIG. 2B that the clinician enters a variable 90 via input device 20. The controller stores this variable in a parameter block 92 and then recomputes the check value (e.g., checksum or CRC) for this parameter. The programmer then redisplays the variable in the parameter block via the output device 22. Thus, if the variable is corrupted before the check value is computed, it will be redisplayed. After the check value is computed and stored in the parameter block 92 the variable is protected by the check value and can be RF transmitted to the medical device 14. Thereafter the scheme of FIG. 2B corresponds to FIG. 2A.

Figure 3:
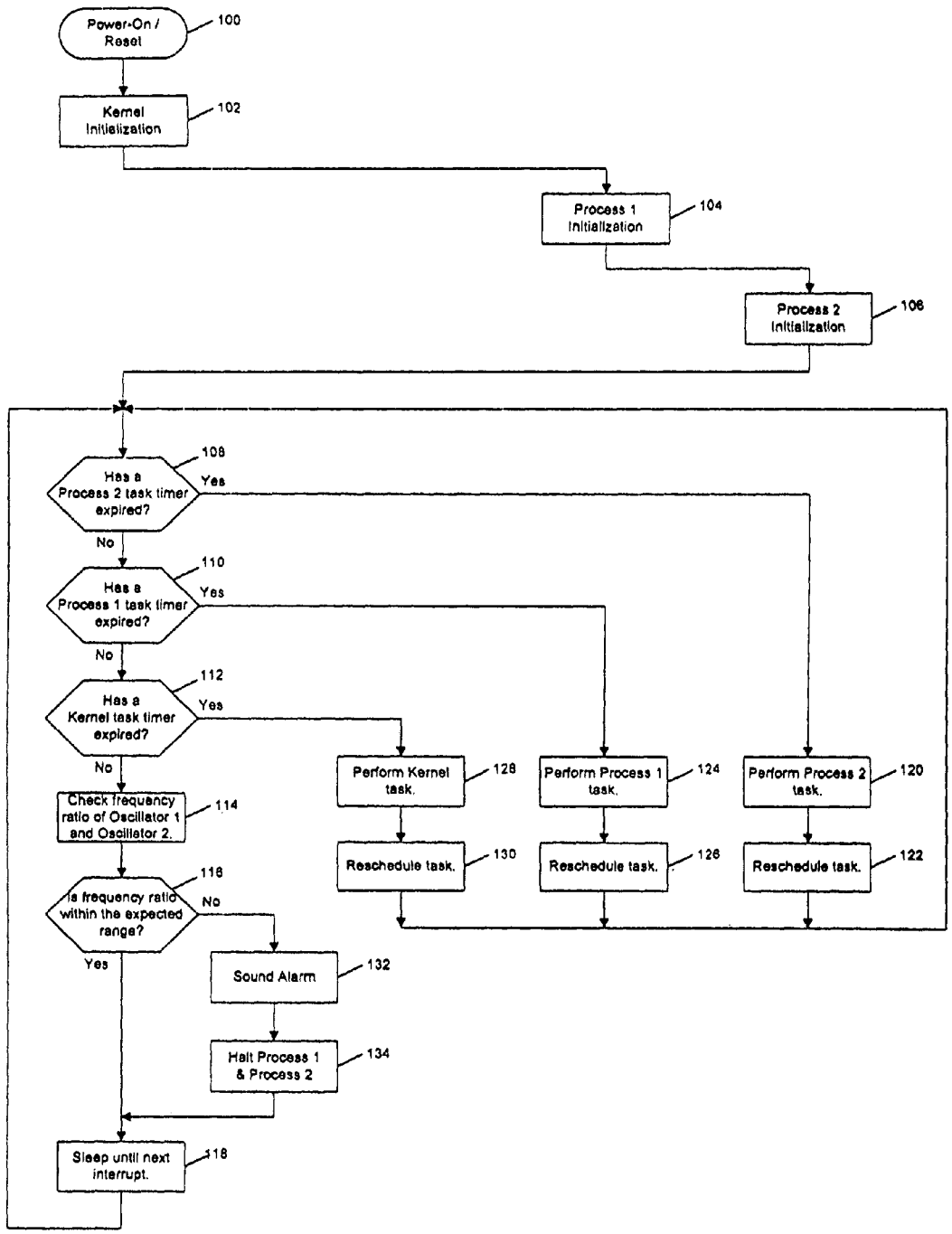
FIG. 3 is a high level flow chart depicting the sequence of Kernel, Process 1, and Process 2 routines by the implanted device microprocessor.

Attention is now directed to FIG. 3 comprising a high level flow chart demonstrating exemplary processing of Kernel, Process 1, and Process 2 functions by the microprocessor 34 (FIG. 1). Execution of the flow chart depicted in FIG. 3 is initiated by block 100 as a consequence of the application of power and/or initiation of a reset function. Subsequently, a Kernel initialization procedure 102 is performed followed by a Process 1 initialization procedure 104 and a Process 2 initialization procedure 106. The processing then proceeds to decision block 108 which asks whether any Process 2 task timer has expired. If NO, then the chart proceeds to decision block 110 which asks whether any Process 1 task timer has expired. If No, then flow proceeds to decision block 112 which inquires whether any Kernel task timer has expired. If NO, then processing proceeds to block 114 to check the frequency ratio of timing oscillators 38 and 40 (FIG. 1). Decision block 116 then inquires whether the frequency ratio is within the expected range. If YES, operation proceeds to block 118 such that the microprocessor goes into a sleep state until the next interrupt with flow then returning to decision block 108.

If the response to decision block 108 is YES, then operation proceeds to block 120 to perform the Process 2 task related to expired timer. After the task is performed, it is rescheduled in block 122 and flow returns to block 108. Similarly, if decision block 110 produces a YES, operation proceeds to block 124 to perform the Process 1 task, the task is rescheduled in block 126, and processing then loops back to decision block 108. Similarly, if decision block 112 produces a YES, the Kernel task is performed (block 128), the task is rescheduled (block 130), and processing loops back to decision block 108. In the event decision block 116 produces a NO, an alarm is initiated (block 132) and Processes 1 and 2 are halted (block 134).

Figures 4A, 4C:
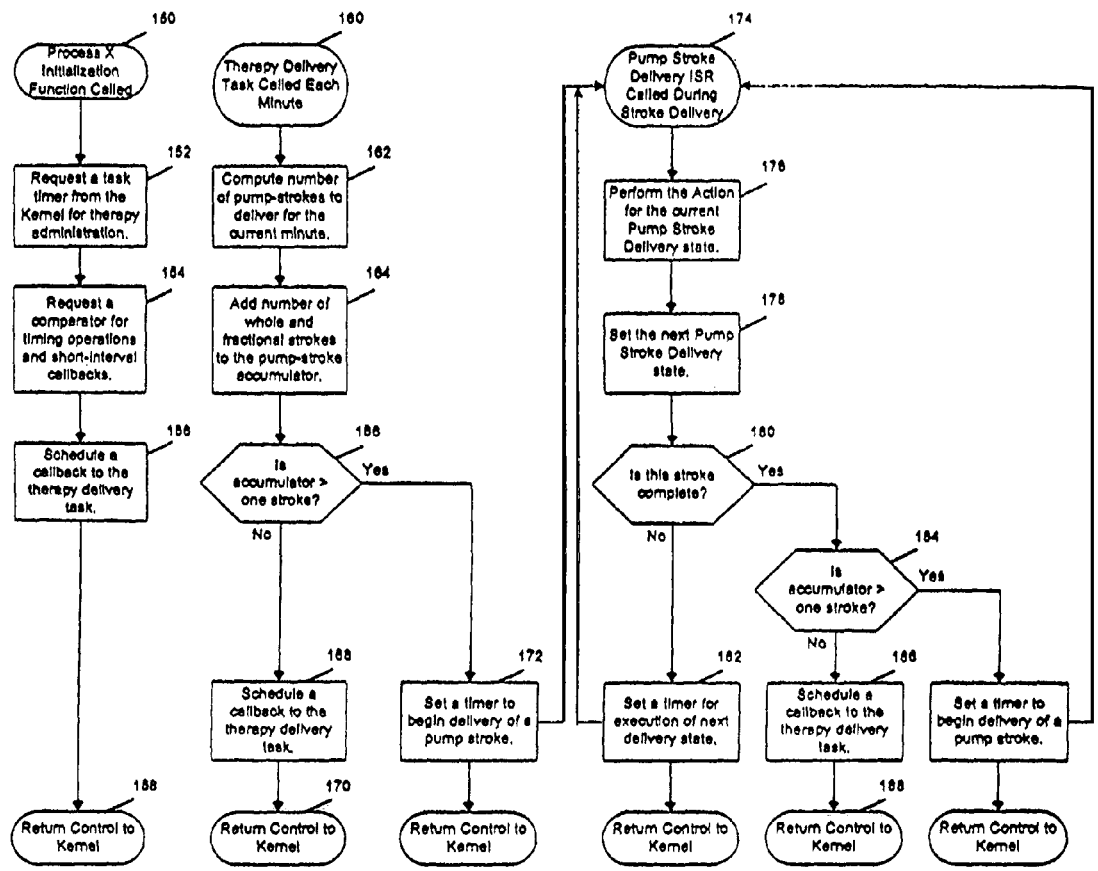
FIGS. 4A and 4C are flow charts where

FIG. 4A depicts a simplified flow chart illustrating how execution of the Kernel can initiate execution of a Process task, e.g., a therapy delivery task. Block 150 represents an initialization function call for Process X. i.e., either Process 1 or Process 2. Block 152 involves requesting a task timer from the Kernel for therapy administration. Block 154 calls for requesting a comparator for timing operations and for short-interval call backs. Block 156 schedules a call back to the therapy delivery task and block 158 represents return of control to the Kernel.

Figure 4B:
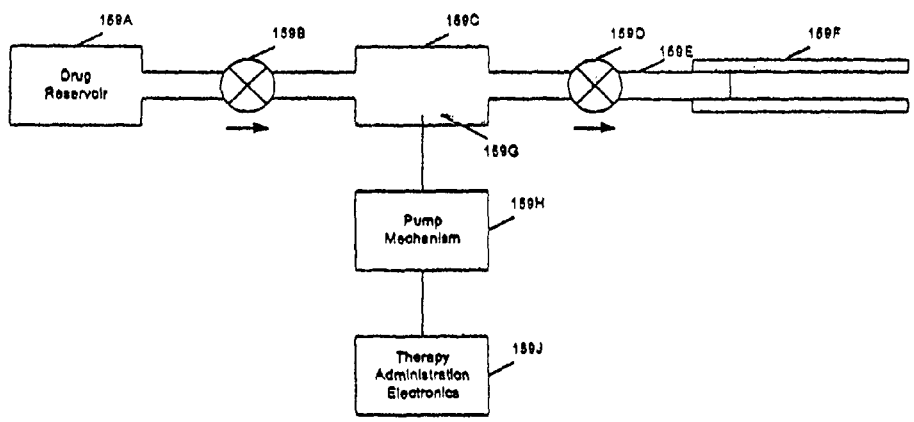

As a specific example, the therapy delivery task can comprise initiating a pump stroke in a drug delivery device of the type schematically represented in FIG. 4B. FIG. 4B depicts a drug reservoir 159A coupled via an upstream check valve 159B to a chamber 159C. The chamber outlet is coupled via check valve 159D to an outlet 159E for delivering drug to a catheter 159F. The chamber 159C contains a diaphragm 159G which can be (1) stroked upwardly to expel a unit volume of drug from the chamber past check valve 159D to the catheter 159F or (2) stroked downwardly to draw drug from the reservoir 159A past check valve 159B into the chamber 159C. The diaphragm 159G is stroked by pump mechanism 159H controlled by therapy administration electronics 159J.

FIG. 4C depicts a flow chart for executing one or more strokes of the pump mechanism 159H. The flow chart of FIG. 4C starts with block 160, representing the initiation of a therapy delivery task which will be assumed to be called once per minute. Block 162 initiates computation of the number of pump strokes to deliver for the current minute. This computation involves adding a quantity to the number of whole and fractional strokes held in a pump-stroke accumulator (block 164). Thereafter, decision block 166 asks if the quantity in the accumulator is greater than one stroke. If NO, block 168 schedules a call back to the therapy delivery task and control returns to the Kernel (block 170). On the other hand, if decision block 166 yields a YES, operation proceeds to block 172 to set a timer for scheduling delivery of a pump stroke prior to returning control to the Kernel.

Block 174 initiates the pump stroke delivery procedure. Block 176 performs the designated action for the current pump stroke delivery state and block 178 sets the next pump stroke delivery state. Decision block 180 asks if the stroke is complete. If NO, a timer is set for execution of next delivery state (block 182) prior to returning to returning to Kernel control.

If decision block 180 produces a YES, then the pump-stroke accumulator is again interrogated (block 184) to determine whether it exceeds one stroke. If NO, a call back to the therapy delivery task is scheduled (block 186) prior to returning control to the Kernel (block 188). On the other hand, if block 184 produces a YES, then block 190 sets a timer to schedule delivery of a pump stroke. Note, that FIG. 4C shows dashed lines from blocks 172, 182, and 190 to represent the action occurring when the respective times expire looping back to block 174.

Figure 5A:
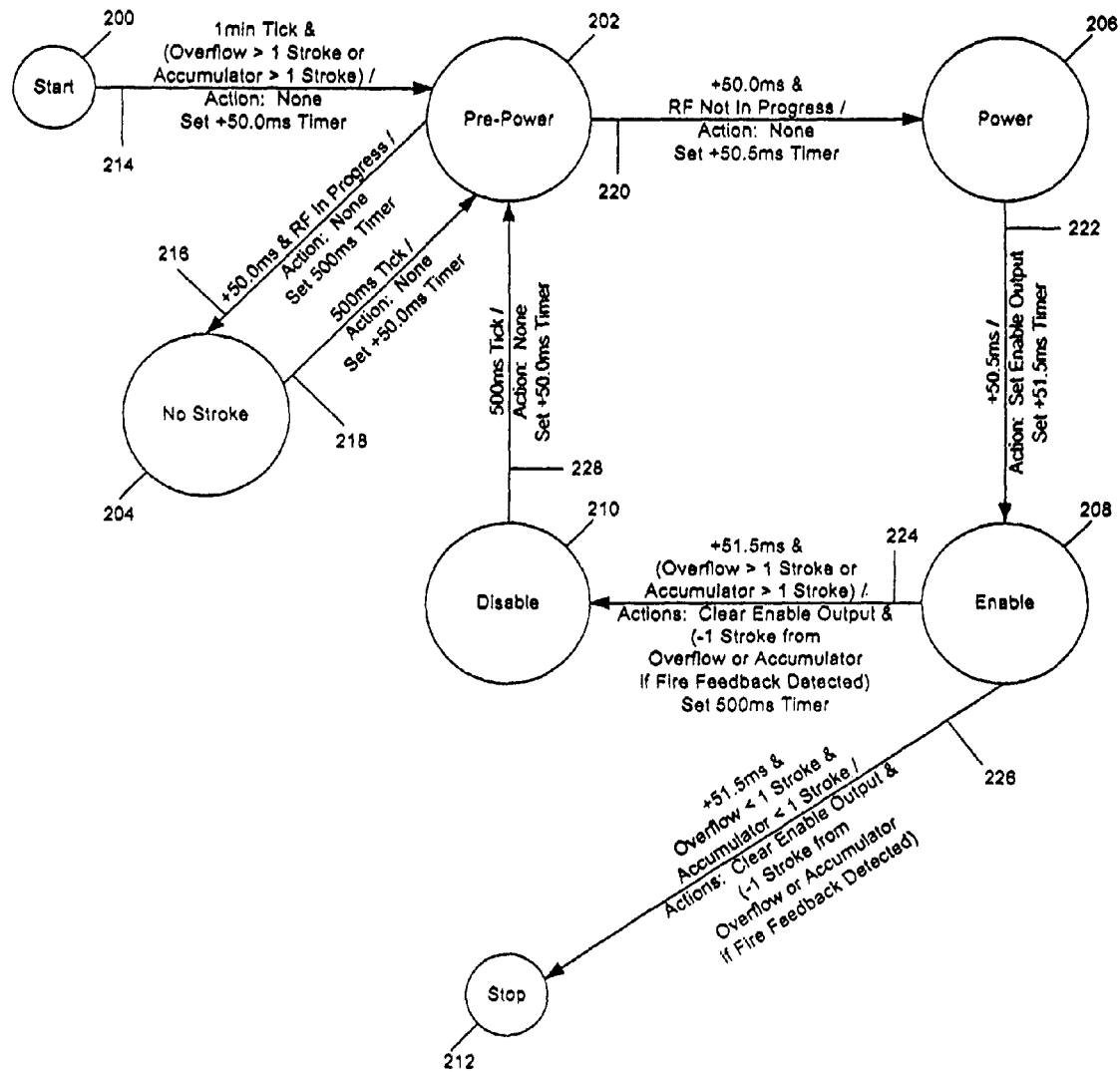
FIG. 5A is a state diagram depicting exemplary Process 1 ("pump enable") states and actions associated with the initiation of a pump stroke.

Note particularly blocks 176 and 178 in FIG. 4C which represents a sequence of actions to be performed to produce pump strokes at the appropriate times. The sequence of actions for an exemplary process, e.g., a pump enable process (Process 1), is illustrated in FIG. 5A which comprises a state diagram in which the state identity is represented by the text in each circle. The arrows connecting the state circles represent the possible state transitions. Note that FIG. 5A depicts the following states:

| | |
|---|---|
| Start | 200 |
| Pre-Power | 202 |
| No Stroke | 204 |
| Power | 206 |
| Enable | 208 |
| Disable | 210 |
| Stop | 212 |

Also note the following state transition arrows in FIG. 5A:

| | |
|---|---|
| Start/Pre-Power | 214 |
| Pre-Power/No Stroke | 216 |
| No Stroke/Pre Power | 218 |
| Pre-Power/Power | 220 |
| Power/Enable | 222 |
| Enable/Disable | 224 |
| Enable/Stop | 226 |
| Disable/Pre Power | 228 |

The text above each arrow represents the conditions which produce the state transition and the text beneath each transition arrow indicates the particular action for each transition. As an example, consider transition arrow 214 extending from Start state 200 to Pre-Power state 202. The text above the transition arrow indicates that the transition occurs on the 1 minute system timer interrupt if the Overflow is greater than 1 OR the Accumulator is greater than 1. When these conditions occur, the text below the transition arrow 214 indicates that the only action taken is to set a timer to +50.0 ms. (The +50 ms indicates that the timer expires 50 ms after the 500 ms system timer interrupt). With the conditions associated with transition arrow 214 are satisfied, then the Pre-Power state 202 is defined.

The condition that produces transition 220 is that the 50.0 ms timer set by transition arrow 214 has expired AND that no RF telemetry (FIGS. 1, 17) is in progress. When this condition occurs, then the only action taken is to set a +50.5 ms timer, in conjunction with the Power state 206 being defined. On the other hand, if the condition associated with transition arrow 220 fails to occur because RF telemetry is in progress, then the condition associated with transition arrow 216 is satisfied. In this case, a 500 ms timer is set and the No Stroke state is defined.

The various conditions and actions for the exemplary pump enable process are clearly shown in FIG. 5A and thus will not be discussed in detail here. It is worth noting though that transition arrow 222 sets an Enable output and transition arrows 224 and 226 clear the Enable outputs.

Figure 5B:
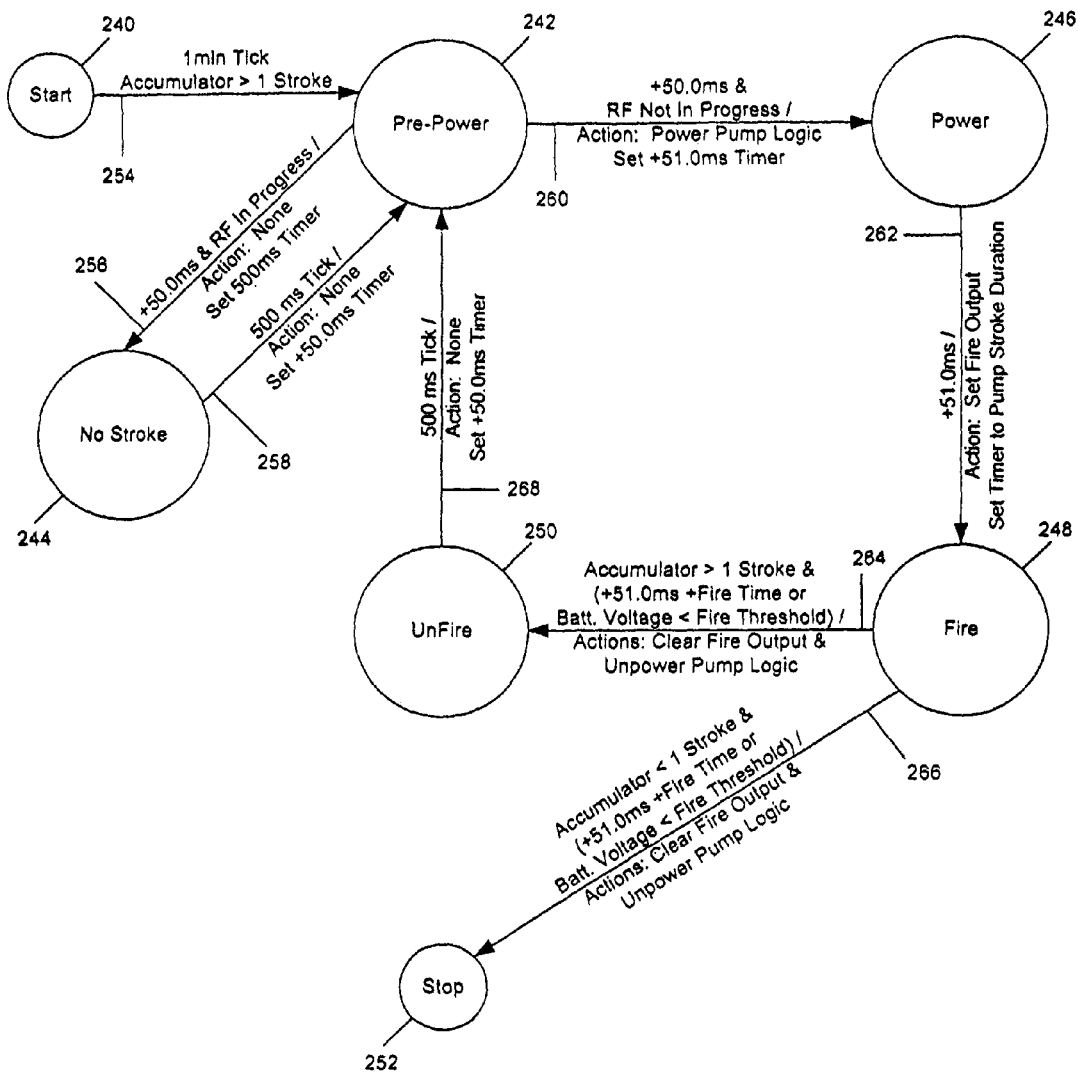
FIG. 5B is a state diagram depicting exemplary Process 2 ("pump fire") states and actions associated with the initiation of a pump stroke.

Whereas FIG. 5A illustrates a state diagram for an exemplary Process 1 (pump enable), FIG. 5B illustrates a similar state diagram for an exemplary Process 2 (pump fire). FIG. 5B depicts the following states:

| | |
|---|---|
| Start | 240 |
| Pre-Power | 242 |
| No Stroke | 244 |
| Power | 246 |

-continued

| | |
|---|---|
| Fire | 248 |
| Unfire | 250 |
| Stop | 252 |

And the following transactions:

| | |
|---|---|
| Start/Pre-Power | 254 |
| Pre-Power/No Stroke | 256 |
| No Stroke/Pre-Power | 258 |
| Pre-Power/Power | 260 |
| Power/Fire | 262 |
| Fire/Unfire | 264 |
| Fire/Stop | 266 |
| Unfire/Pre-Power | 268 |

The various conditions and actions for the exemplary pump fire process are shown clearly in FIG. 5B and thus will not be discussed in detail here. It is pointed out, however, that transition 262 sets a Fire output and transitions 264 and 266 clear the Fire outputs.

Figure 6A:
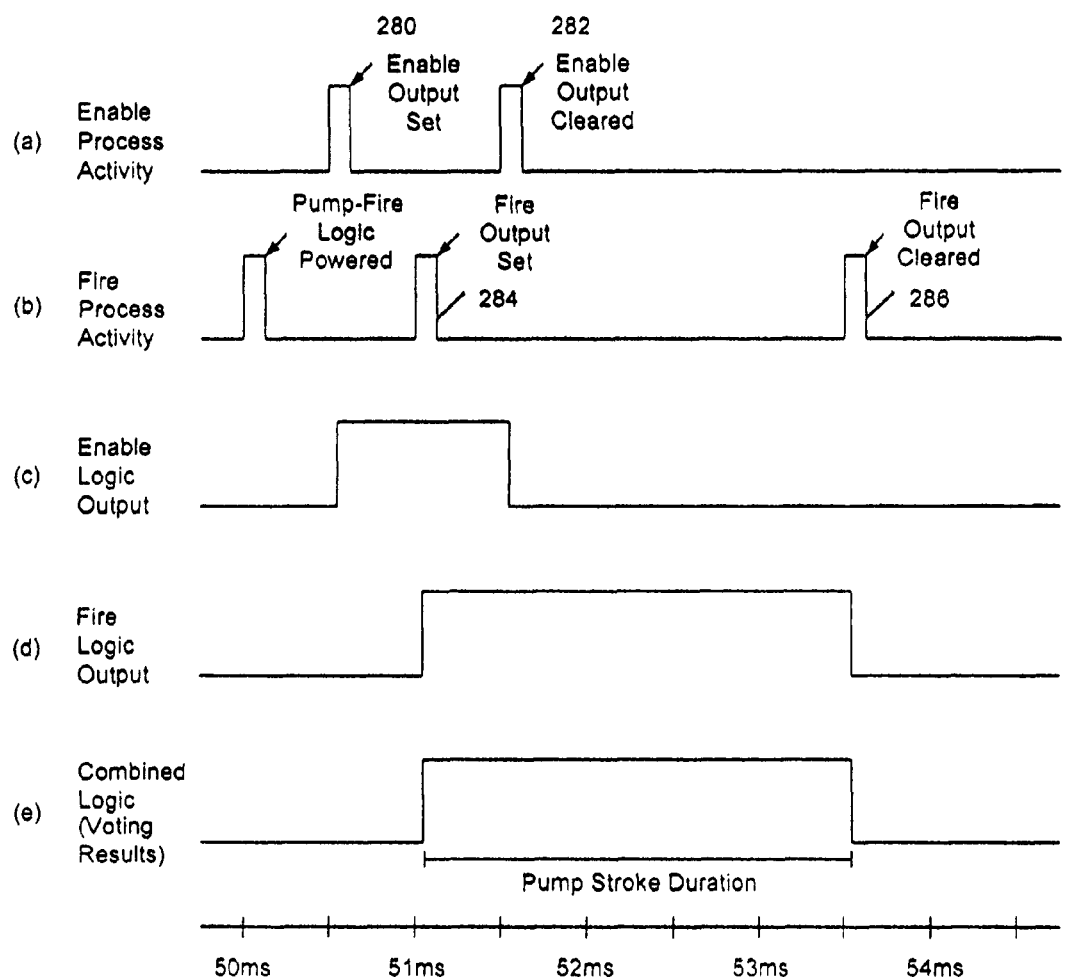
FIG. 6A is an exemplary timing chart indicating how Process 1 and Process 2 output signal components can be combined in combinatorial logic to produce a therapy control output signal for controlling an implantable device therapy administration subsystem.

FIG. 6A is an exemplary timing chart illustrating how Enable and Fire outputs produced in FIGS. 5A and 5B, respectively, can be applied to combinatorial logic to produce a therapy control output signal. Line (c) of FIG. 6A depicts the Enable output generated as a consequence of the actions performed in Process 1 (FIG. 5A) and shown in Line (a) of FIG. 6A as an Enable set pulse 280 and an Enable clear pulse 282. Line (d) depicts the Fire output produced as a consequence of the actions performed in Process 2 (FIG. 5B) and shown as a Fire set pulse 284 and a Fire clear pulse 286. Line (e) of FIG. 6A depicts an exemplary therapy control output signal produced by combinatorial logic 56 (FIG. 1) in response to the Process 1 and Process 2 components (FIG. 6A, lines a, b).

Figure 6B:
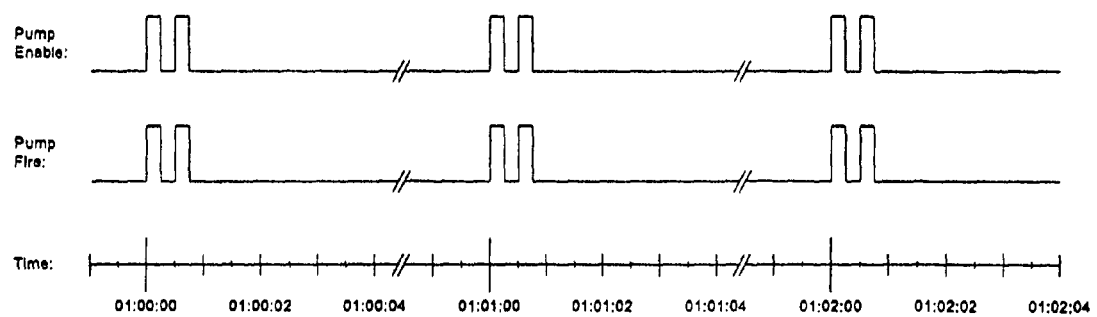
FIGS. 6B and 6C illustrate alternative exemplary time charts.

FIG. 6B illustrates an alternative exemplary timing chart in which the outputs of the two processes are time coordinated. Assume, for example, a situation in which the pump mechanism has a stroke volume of 1 microliter and can be fired every half second. If a clinician has filled the implanted device with a drug that has a 25 mg/mL concentration and has programmed a 36 mg/day delivery rate, ten strokes per minute are required to satisfy the demand. FIG. 6B depicts a situation in which both processes vote at the beginning of each minute and half a second after the beginning of each minute.

Redundancy can be achieved even if the processes use the same algorithm or algorithms in order to make therapeutic decisions. However, the use of different algorithms is preferable, because it has a better chance at catching defects that might exist in the software after system verification and validation. If these processes do use the same algorithm, such a defect could manifest itself in each process and result in an error in therapy. However, if two different algorithms are used, this same defect would most likely manifest itself in only one of the processes. Thus, the other process would be able to prevent a therapeutic error.

Figure 6C:

For an implantable pump, the enable process could be such that it enables, i.e., permits pump activation, for some amount of time for each delivery interval to limit the pump's duty cycle. In such a scheme, the duration of the enable would be set long enough so that only the maximum programmed rate during the day could be delivered. Thus, the enable duration constitutes a rate limit where the limit is typically set to the maximum basal rate of drug delivery. If the implanted drug pump contains a supplemental delivery means, the rate limit could be set to the maximum of the sum of the two delivery means (basal+supplemental). Alternatively, the limit could be increased during the periods of supplemental delivery. The vote timing for these schemes is depicted in FIG. 6C. It should be noted that the enable is longer than the duration of the fire pulse train. This is a result of the implanted device delivering drug at a rate slower than the maximum rate that can be delivered at some point during the day.

Figure 7A:
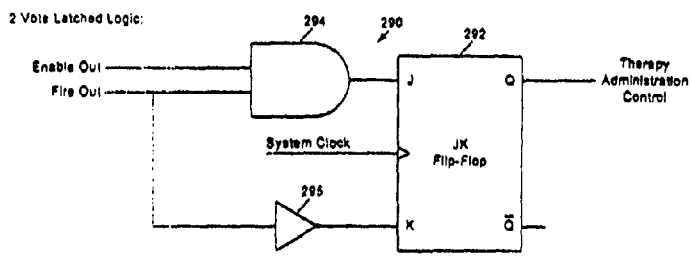
FIGS. 7A, 7B, 7C, respectively depict different exemplary forms of combinatorial logic, or voting circuits, for producing a therapy control output signal.

FIG. 7A depicts an exemplary combinatorial logic 290 for responding to the Process components depicted in FIG. 6, lines (a), (b) to produce the therapy control output signal of line (e). Logic 290 is comprised of a J-K flip-flop 292. The two Process components (i.e., Enable and Fire out) are applied to AND gate 294 whose output is connected to the J input of flip-flop 292. The Fire out input is also coupled through inverter 295 to the K input. Thus, flip-flop 292 is set via the J input when lines (c) and (d) of FIG. 6 are both true. The flip-flop will then be reset by the Fire clear output 286.

Figure 7B:
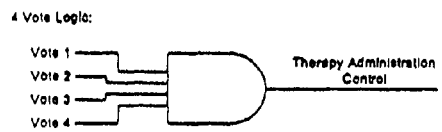

The combinatorial logic 290 of FIG. 7A acts as a voting device which requires concurrence by the two inputs to produce an output signal for controlling therapy administration. Although the exemplary system described herein (FIG. 1) only shows the execution of two separate processes for independently producing two output components for application to the combinatorial logic, it should be understood that alternative embodiments can execute more than two independent processes. In such embodiments, the combinatorial logic can be implemented to require either a unanimous vote of the multiple process output components or that the components merely exceed a certain threshold. For example, assume a system in which four separate processes are executed to produce four independent output components. In such a case, the combinatorial logic can be implemented by a simple AND gate as shown in FIG. 7B which requires that all of the voting components agree in order to produce an output signal to control therapy administration.

Figure 7C:
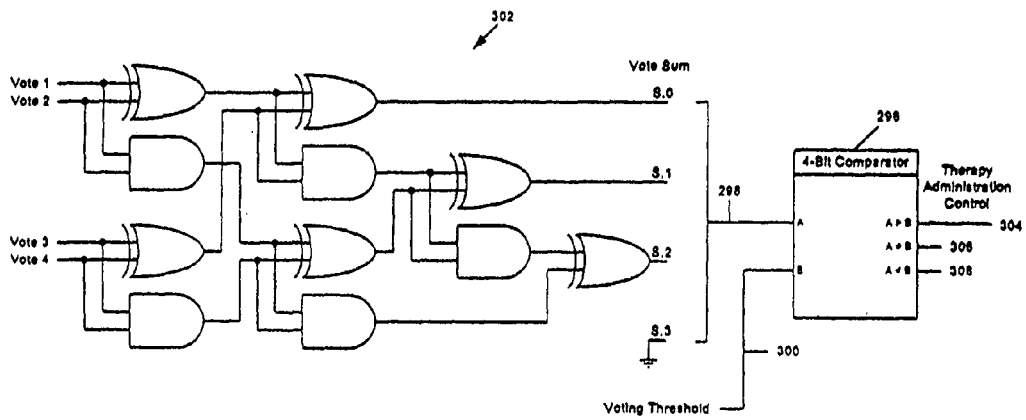

However, for some applications it may be appropriate to accept a lower than unanimous threshold for controlling therapy administration. For example, it may be acceptable in certain applications to change a therapy in response to three out of four voting components, i.e., a 75% threshold. An exemplary combinatorial logic 298 is shown in FIG. 7C which uses a comparator 296 having a voting input terminal 298 and a threshold input terminal 300. Gating circuitry 302 couples the multiple voting components to the voting input terminal 298. A voting threshold signal is applied to threshold terminal 300. The comparative 296 functions to provide an output signal on terminal 304 if the voting components exceed the threshold, on 306 if the voting components equal the threshold or on terminal 308 if the voting components are less than the threshold.

Although a limited number of combinatorial logic implementations have been shown herein, it should be recognized that many other variations can be used to produce a therapy control output signal which depends upon the nature of the voting input components.

From the foregoing, it should now be appreciated that a medical system has been disclosed herein including an implantable medical device configured to realize the benefits of redundancy by executing multiple software processes on a common microprocessor. Although only a limited number of embodiments have been described, it should be recognized that modifications and variations may readily occur to those skilled in the art coming within the spirit of the invention and the intended scope of the appended claims.

The invention claimed is:

1. An implantable medical device including:
   a therapy administration subsystem; and
   a control subsystem configured to produce a therapy control output signal for controlling said therapy administration subsystem, said control subsystem comprising:
      a microprocessor; and
      means for causing said microprocessor to separately execute at least two separate software processes which process the same data set to respectively produce separate therapy control output components; and
      combinatorial logic means responsive to said separate output components for producing said therapy control output signal;
      wherein said combinatorial logic means is responsive to all of said output components and requires a unanimous vote of the output components to produce said therapy control output signal;
      wherein said two software processes execute different algorithms.

2. The medical device of claim 1 wherein said therapy administration subsystem includes a pump mechanism actuatable to deliver a drug from a drug reservoir to a drug outlet.

3. The medical device of claim 1 wherein said therapy administration subsystem includes a pump mechanism actuatable to produce a pump stroke for delivering a unit volume of drug to a drug outlet; and wherein
   said therapy control output signal controls the rate of pump strokes.

4. The medical device of claim 3 wherein a first of said processes produces an output component comprising one or more fire command pulses for initiating pump strokes, and wherein
   a second of said processes produces an output component comprising an enable signal for limiting the rate at which said pump strokes are produced.

5. The medical device of claim 4 wherein said second process produces an enable signal which limits the rate of pump strokes to a basal drug delivery rate during a defined time interval.

6. An implantable medical device including:
   a therapy administration subsystem;
   a control subsystem configured to produce a therapy control output signal for controlling said therapy administration subsystem, said control subsystem comprising
      a microprocessor, and
      means for causing said microprocessor to separately execute at least two separate software processes to respectively produce separate therapy control output components; and
   combinatorial logic means responsive to said separate output components for producing said therapy control output signal;
   wherein the microprocessor includes a first oscillator means for producing a primary clock and second oscillator means functioning to verify the frequency of said primary clock such that a single oscillator fault is prevented from affecting the time base of both processes.

7. A method of operating an implantable medical device to safely administer therapy, said method including:
   providing a therapy administration subsystem;
   providing a control subsystem for producing a therapy control output signal to control said therapy administration subsystem;
   configuring said control subsystem with a microprocessor;
   causing said microprocessor to separately execute at least two software processes which process the same data set to respectively produce separate therapy control output components; and
   responding to said output components requiring a unanimous vote of the output components to produce said output signal for controlling said therapy administration subsystem such that a single point software decision to administer or change a therapy is prevented;
   wherein said at least two software processes execute different algorithms.

8. The method of claim 7 wherein said therapy administration subsystem includes an actuatable pump mechanism and wherein said output signal actuates said mechanism to transfer a unit volume of medication from a reservoir to a body site.

9. The method of claim 7 wherein a first of said processes produces an output component comprising one or more fire command pulses for initiating pump strokes, and wherein
   a second of said processes produces an output component comprising an enable signal for limiting the rate at which said pump strokes are produced.

10. A method of operating an implantable medical device to safely administer therapy, the implantable medical device being controllable in response to processor output components, said method including:
    executing separate software processes which process the same data set to produce respective output components for initiating a pump stroke to deliver a unit volume of medication to the patient only when all of said output components represent a unanimous vote to administer the therapy, the separate processes including
       a first process that produces an output component comprising one or more fire command pulses, and
       a second process that produces an output component comprising an enable signal for limiting the rate at which said pump strokes are produced;
    wherein the separate software processes use different algorithms.

11. The method of claim 10 wherein said second process produces an enable signal which limits the rate of pump strokes to a basal drug delivery rate during a defined time interval.

12. The method of claim 10 wherein said enable signal is set to provide a rate limit for drug delivery.

13. The method of claim 12 wherein the rate limit is the maximum basal rate of drug delivery.

14. The method of claim 12 wherein the rate limit is the maximum of the sum of basal and supplemental rates of drug delivery.

15. The method of claim 12 wherein the rate limit increases during periods of supplemental delivery.

16. The method of claim 10 wherein the outputs of the separate software processes are time coordinated.

* * * * *